US012758210B2

(12) United States Patent
Federspiel et al.

(10) Patent No.: US 12,758,210 B2
(45) Date of Patent: Oct. 13, 2026

(54) AUTOMATIC RELEASE OF A NEAR BONE SUTURE BUTTON FROM A BUTTON INSERTER

(71) Applicant: Acumed LLC, Hillsboro, OR (US)

(72) Inventors: Joshua P. Federspiel, Portland, OR (US); Ann Nicole Santich, Portland, OR (US); David William Vanvleet, Hillsboro, OR (US); Gretchen Hinton, Hillsboro, OR (US); Tristan Sommers, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 237 days.

(21) Appl. No.: 18/786,031

(22) Filed: Jul. 26, 2024

(65) Prior Publication Data

US 2024/0382190 A1 Nov. 21, 2024

Related U.S. Application Data

(62) Division of application No. 17/245,335, filed on Apr. 30, 2021, now Pat. No. 12,064,102.

(Continued)

(51) Int. Cl.
*A61B 17/04* (2006.01)

(52) U.S. Cl.
CPC .. *A61B 17/0401* (2013.01); *A61B 2017/0404* (2013.01); *A61B 2017/0409* (2013.01)

(58) Field of Classification Search
CPC ............ A61B 17/0401; A61B 17/0469; A61B 17/0483; A61B 2017/0409;

(Continued)

(56) References Cited

U.S. PATENT DOCUMENTS 5,921,986 A * 7/1999 Bonutti ................ A61B 17/683
606/57
6,013,083 A * 1/2000 Bennett ................. A61F 2/0805
606/232

(Continued)

FOREIGN PATENT DOCUMENTS

| | | | |
|---|---|---|---|
| JP | 2022-550839 | A | 12/2022 |
| KR | 20120059776 | A | 6/2012 |
| WO | WO 2021/222698 | A1 | 11/2021 |

OTHER PUBLICATIONS

Japanese Office Action corresponding to related Japanese Patent Application No. 2022-550839 dated Sep. 17, 2024, 6 pages.

(Continued)

*Primary Examiner* — Dianne Dornbusch
(74) *Attorney, Agent, or Firm* — Knobbe, Martens, Olson & Bear, LLP

(57) ABSTRACT

A button inserter and system are disclosed that enable easily and effectively deploying a near bone suture button from the button inserter when implementing the suture button technique. To deploy the near bone button, with a far bone button deployed from the button inserter and against the far bone, the button inserter's handle may be translated away from the deployed far bone button. Translating the handle changes a position of a carriage body within a channel of the handle thereby compressing a spring. Protrusions on the carriage body may be forced through notches in the handle, which thereby alters an orientation of the carriage and releases the compressed spring, which applies force to the carriage body. The combination of force induces the carriage to rotate, which thereby releases the near bone button from the carriage. A free end of suture also releases from the carriage.

15 Claims, 13 Drawing Sheets

Related U.S. Application Data

(60) Provisional application No. 63/018,825, filed on May 1, 2020.

(58) Field of Classification Search
CPC .... A61B 2017/0404; A61B 2017/0411; A61B 2017/049
See application file for complete search history.

(56) References Cited

U.S. PATENT DOCUMENTS

| | | | | |
|---|---|---|---|---|
| 9,226,743 | B2 | 1/2016 | Dreyfuss et al. | |
| 9,642,610 | B2 * | 5/2017 | Albertorio | A61B 17/0401 |
| 11,109,855 | B2 | 9/2021 | Shoshtaev et al. | |
| 12,064,102 | B2 | 8/2024 | Federspiel et al. | |
| 2002/0019634 | A1 * | 2/2002 | Bonutti | A61B 17/82 606/57 |
| 2005/0192632 | A1 * | 9/2005 | Geissler | A61F 2/0811 606/232 |
| 2008/0119874 | A1 | 5/2008 | Merves | |
| 2009/0043318 | A1 * | 2/2009 | Michel | A61B 17/0401 606/232 |
| 2010/0305576 | A1 | 12/2010 | Ferguson | |
| 2011/0022061 | A1 * | 1/2011 | Orphanos | A61B 17/0469 606/232 |
| 2012/0123474 | A1 * | 5/2012 | Zajac | A61B 17/86 606/232 |
| 2013/0053897 | A1 * | 2/2013 | Brown | A61B 17/8861 606/232 |
| 2014/0277125 | A1 | 9/2014 | Spivey | |
| 2014/0277194 | A1 * | 9/2014 | Mattchen | A61B 17/68 606/328 |
| 2017/0135688 | A1 | 5/2017 | Branthover | |
| 2017/0156717 | A1 | 6/2017 | Triplett et al. | |
| 2017/0290579 | A1 * | 10/2017 | Norton | A61B 17/0401 |
| 2017/0303907 | A1 | 10/2017 | Sengun et al. | |
| 2018/0085110 | A1 | 3/2018 | Earhart et al. | |
| 2018/0116659 | A1 | 5/2018 | Walters | |
| 2018/0249998 | A1 * | 9/2018 | Chavan | A61B 17/0401 |
| 2020/0100781 | A1 | 4/2020 | Brunsvold et al. | |
| 2021/0298738 | A1 * | 9/2021 | Taylor | A61B 17/0401 |
| 2022/0142635 | A1 * | 5/2022 | Bachmaier | A61B 17/0401 |

OTHER PUBLICATIONS

International Search Report corresponding to related International Patent Application No. PCT/US2021/030082 mailed Aug. 16, 2021, 3 pages.

International Written Opinion corresponding to related International Patent Application No. PCT/US2021/030082 mailed Aug. 16, 2021, 5 pages.

International Preliminary Report corresponding to related International Patent Application No. PCT/ US2021/030082 mailed Nov. 10, 2022, 7 pages.

Extended European Search Report corresponding to related European Patent Application No. 21795444.5 dated May 10, 2024, 6 pages.

* cited by examiner

AUTOMATIC RELEASE OF A NEAR BONE SUTURE BUTTON FROM A BUTTON INSERTER

PRIORITY CLAIM

The present application is a divisional of U.S. patent application Ser. No. 17/245,335, filed Apr. 30, 2021, now U.S. Pat. No. 12,064,102, which claims priority to and the benefit of U.S. Provisional Application 63/018,825, filed May 1, 2020, the entireties of each of which are herein incorporated by reference.

BACKGROUND

Patients may sometimes suffer injuries that require securing a first, or near, bone to a second, or far, bone in order to help the patient recover from the injury. Injuries to the ankle joint may be one such type of injury. The ankle joint is composed of two bones, the tibia and fibula, which are held together by the distal tibiofibular syndesmosis. In some instances, such as after ankle injuries, the syndesmosis can be torn, leaving a gap between the tibia and fibula. Syndesmotic injuries should be repaired if found torn or unstable in order to prevent ankle instability and subsequently reduce the risk of ankle osteoarthritis.

One method to secure a near bone to a far bone is the suture button technique. The suture button technique includes deploying a bone-securing construct that includes a first (e.g., far bone) button coupled to a second (e.g., near bone) button with suture. The suture may be tensioned to secure the near bone to the far bone. For example, to repair syndesmotic injuries, the suture button technique involves two buttons that hold the fibula (e.g., near bone) and tibia (e.g., far bone) together with suture that connects the two buttons through a drilled bone hole in the fibula and tibia. The far bone button may be inserted through the drilled bone hole to secure the tibia while the near bone button secures the fibula. The buttons are typically put into place with a needle and pull-through sutures or with a button inserter.

Typical button inserters require manual removal of the near bone button (e.g., the one not inserted through the bone) from the inserter. This can be a multiple step process of loosening or unwrapping suture, and then lifting the near bone button from the handle, which can be cumbersome and time-consuming for surgeons. Accordingly, a button inserter designed to quickly and easily deploy a near bone button is desired.

SUMMARY

The present application provides a new and innovative button inserter and system having a mechanism for deploying and releasing a near bone button from the inserter. After deploying a far bone button from the inserter, a surgeon may deploy the near bone suture button and accompanying suture in a suture button construct from the button inserter in a single motion by translating the button inserter. As such, the provided button inserter more effectively and efficiently deploys the near bone button than typical button inserters.

In an example, a system for suture button insertion includes a suture button construct and a suture button inserter. The suture button construct includes a far bone button joined by suture to a near bone button. The suture button inserter includes a handle, a tube, a carriage, and a spring. A portion of the handle defines a channel, a first notch, and a second notch. The tube extends from the handle. The carriage includes a body. A button post, a first suture post, and a second suture post each extend from the body. A first protrusion and a second protrusion each extend from the body. In a pre-deployment configuration of the suture button inserter, a portion of the body including the first and second protrusions is positioned within the channel of the handle such that the portion of the body may translate within the channel. A first end of the spring is in contact with a portion of the handle and a second end of the spring is in contact with the body of the carriage. Translating the carriage towards the first end of the spring compresses the spring. At least part of the portion of the body within the channel may be removed from the channel when the first and second protrusions are aligned with the first and second notches of the handle. In the pre-deployment configuration of the suture button inserter, the near bone button is positioned against the button post in the far bone button is positioned at an end of the tube such that the suture is taut between the near bone button and the far bone button.

In another example, a suture button inserter includes a handle, a carriage, and a spring. A portion of the handle defines a channel, a first notch, and a second notch. The carriage includes a body. A button post, a first suture post, and a second suture post each extend from the body. A first protrusion and a second protrusion each extend from the body. In a pre-deployment configuration of the suture button inserter, a portion of the body including the first and second protrusions is positioned within the channel of the handle such that the portion of the body may translate within the channel. A first end of the spring is in contact with a portion of the handle and a second end of the spring is in contact with the body of the carriage. Translating the carriage towards the first end of the spring compresses the spring. At least part of the portion of the body within the channel may be removed from the channel when the first and second protrusions are aligned with the first and second notches of the handle.

In another example, a suture button construct includes a far bone button joined by suture to a near bone button. A method for deploying the suture button construct from a button inserter includes inserting the far bone button through a bone hole via the button inserter. The far bone button may then be deployed from the button inserter. The button inserter may then be translated away from the deployed far bone button which thereby deploys the near bone button from the button inserter.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 1:
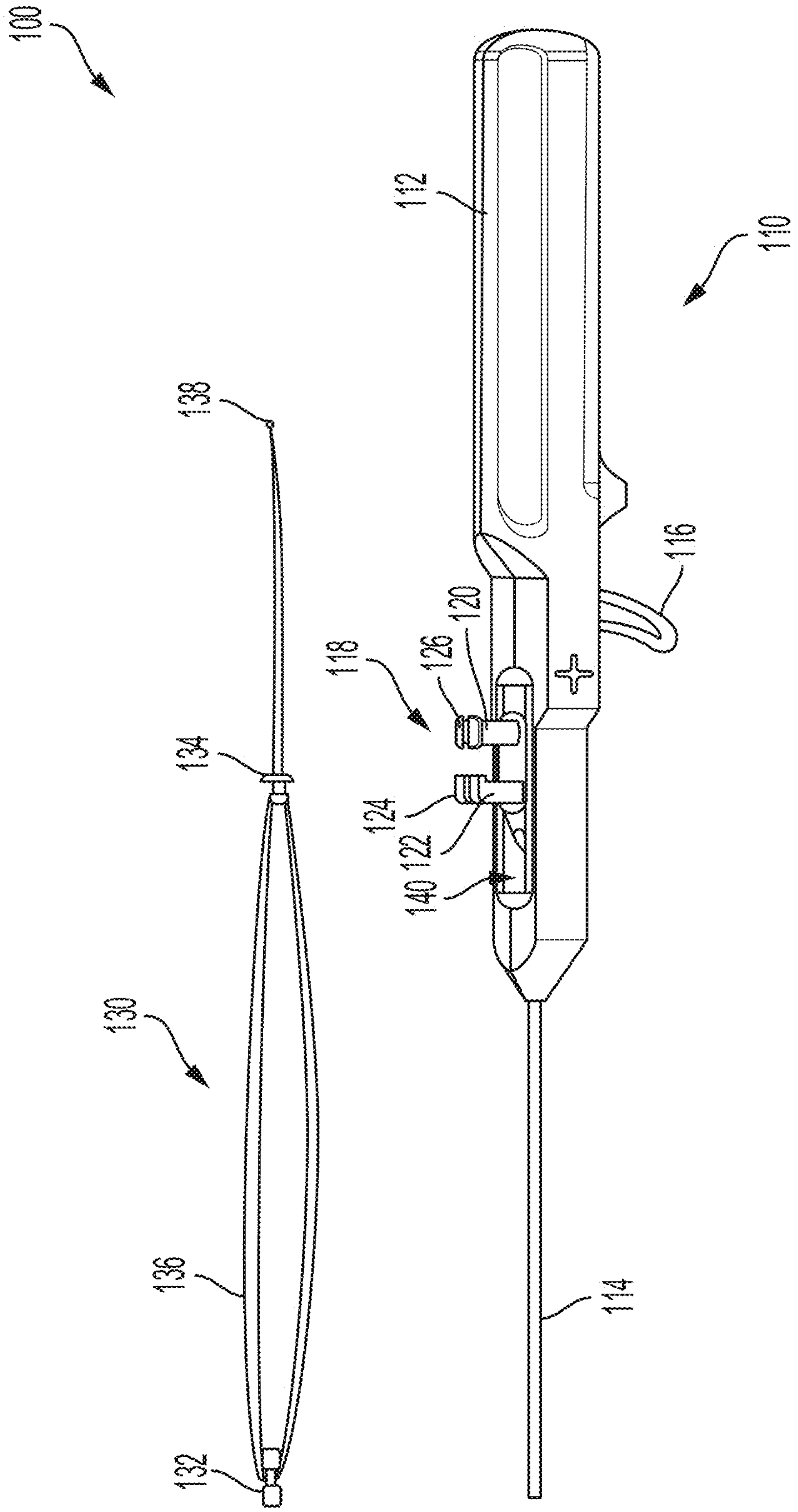
FIG. 1 illustrates an exploded perspective view of a suture button inserter system including a suture button inserter and a suture button construct, according to an aspect of the present disclosure.

A button inserter, system, and method are disclosed that enable surgeons, or any other suitable healthcare provider, to easily and effectively deploy a near bone button from the button inserter when implementing the suture button technique, such as to repair syndesmosis injuries in ankles. The provided button inserter includes a handle defining a channel. The handle may also define a pair of notches at an opening of the channel. A tube may extend from the handle that is part of the far bone suture button deployment mechanism of the button inserter.

The provided button inserter additionally includes a carriage. The carriage may include a body portion and a number of posts extending from the body portion. For instance, the carriage may include one or more button posts and one or more suture posts. The one or more button posts secure a positioning of a near bone button to maintain tension in the suture prior to deployment, as described more below. The one or more suture posts secure a free end of the suture prior to deployment, as described more below. The carriage may include at least two protrusions extending from the body portion. A portion of the carriage including the protrusions may be positioned within the handle's channel prior to deployment and may translate within the channel. The protrusions help prevent this carriage portion from exiting the channel until the protrusions are aligned with the handle's notches, at which point the protrusions can be translated through the notches so that the carriage may fully or partially exit the channel.

A spring, or other suitable resilient member, is present within the handle's channel. One end of the spring is in contact with the handle while the other end of the spring is in contact with the carriage. In this way, a position of the carriage within the channel may change with respect to the handle to compress the spring, or conversely, a compressed spring may apply force to the carriage as the compressed spring releases.

A suture button construct may be loaded onto the provided button inserter for deployment in a patient. The suture button construct includes a far bone button joined by suture to a near bone button. In a pre-deployment configuration, the far bone button is positioned at an end of the button inserter's tube, the near bone button is positioned against the carriage's button post(s), and the suture between the far and near bone buttons is tensioned. The suture's free end may be wrapped around the suture posts in a way that allows the wrapped suture to automatically release from the suture posts upon deployment of the near bone button. For instance, the suture's free end may be wrapped around the suture posts according to the wrapping method described below. The provided wrapping method helps prevent knot formation in the suture as it unwinds and thereby helps eliminate the need for a surgeon to manually unwind the suture.

To deploy the suture button construct from the provided button inserter, a surgeon may transport the far bone button through a bone hole via the button inserter and actuate a mechanism for deploying the far bone button. For example, the surgeon may pull a trigger that translates a rod within the button inserter's tube to force the far bone button away from the tube and thereby deploy the far bone button. With the far bone button deployed from the button inserter and against the far bone, the surgeon may translate the button inserter's handle away from the deployed far bone button (e.g., at least partially back through the bone hole). The tension in the suture between the far and near bone buttons prevents the carriage from translating with the handle. As such, translating the handle compresses the spring and increases tension in the suture, which each exert counteracting forces on the carriage. Translating the handle also changes a position of the carriage body within the handle's channel.

Once the carriage body's protrusions are aligned with the handle's notches, the combination of the tension in the suture and the force exerted on the carriage body by the spring induces the carriage to change orientation with the protrusions moving through the notches. For example, the carriage may rotate ninety degrees from a horizontal orientation to a vertical orientation. In some instances, a surgeon may help force the protrusions through the notches. For example, the surgeon may use a thumb to push upward on the carriage's suture posts (or the suture wrapped around the suture posts) to force the protrusions through the notches. The change in orientation of the carriage releases the near bone button from the carriage. For instance, the button post(s) no longer restrains the near bone button against tension in the suture with the carriage in the vertical position. Further, the vertically positioned carriage loosens the suture tension on the near bone button thereby releasing it from the carriage. The free end of the suture also releases from the suture posts. In this way, a surgeon may deploy the near bone suture button and accompanying suture in a suture button construct from the button inserter in a single motion by translating the button inserter. The surgeon may then tension the deployed suture and secure the deployed near bone button against the near bone by tying off the suture.

FIG. 1 illustrates an example suture button insertion system 100 including a suture button construct 130 and a button inserter 110. In at least some aspects, the suture button construct 130 includes a far bone button 132 (e.g., FIG. 8) joined by suture 136 to a near bone button 134 (e.g., FIG. 9). In some instances, a free end of the suture 136 may include a knot 138.

The example button inserter 110 includes a handle 112. In various aspects, a tube 114 extends from the handle 112. A rod 302 (FIG. 3) may be positioned within the tube 114. The rod 302 may be operably coupled to a trigger 116 such that actuating the trigger 116 translates the rod 302 within the tube 114. The handle 112 defines a channel 140 (best illustrated in FIG. 7). In various aspects, the handle 112 further defines at least two notches 704A and 704B (FIG. 7) at an opening of the channel 140.

Figure 4A:
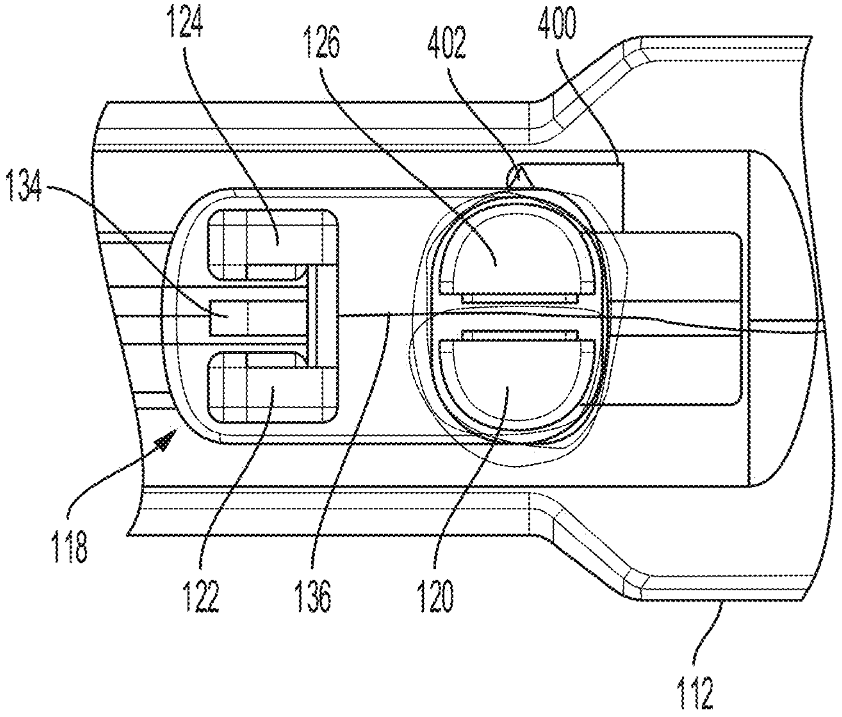
FIG. 4A illustrates a magnified view of the top view of FIG. 3, according to an aspect of the present disclosure.
Figure 4B:
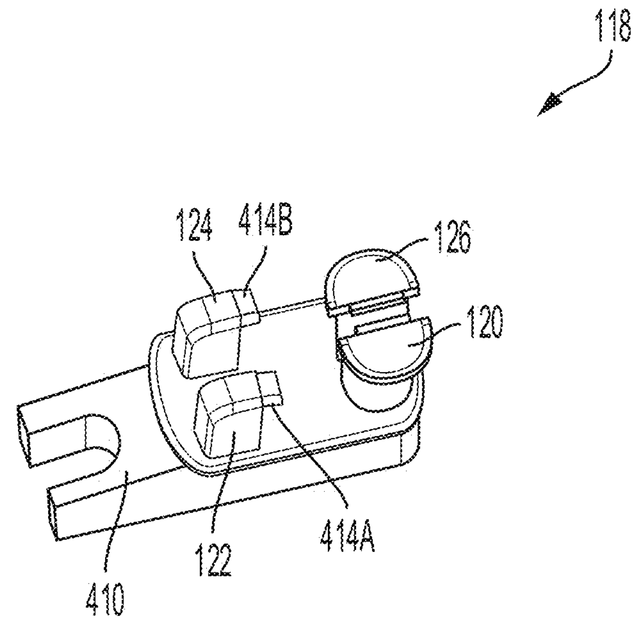
FIG. 4B illustrates a perspective view of the carriage of the suture button inserter of FIG. 1, according to an aspect of the present disclosure.

The example button inserter 110 further includes a carriage 118. FIG. 4B illustrates a perspective view of an example carriage 118. The carriage 118 may include a body 410. In various aspects, at least two protrusions 412A and 412B (FIG. 7) may extend from the body 410. A portion of the body 410 of the carriage 118 (e.g., the portion including the protrusions 412A and 412B) may be positioned within the channel 140 of the handle 112. The protrusions 412A, 412B may help prevent the portion of the body 410 of the carriage 118 from exiting the channel 140 in a pre-deployment configuration of the suture button insertion system 100. In various aspects, the carriage 118 may include one or more button posts 122, 124 extending from the body 410 of the carriage 118. In some aspects, a button post 122, 124 may include a lip 414A, 414B. While a button post 122 and a button post 124 are shown in the illustrated example, in other examples, the carriage 118 may include a single, suitable button post or more than two button posts. In various aspects, the carriage 118 may include one or more suture posts 120, 126. While a suture post 120 and a suture post 126 are shown in the illustrated example, in other examples, the carriage 118 may include a single, suitable suture post or more than two suture posts.

Figure 2:
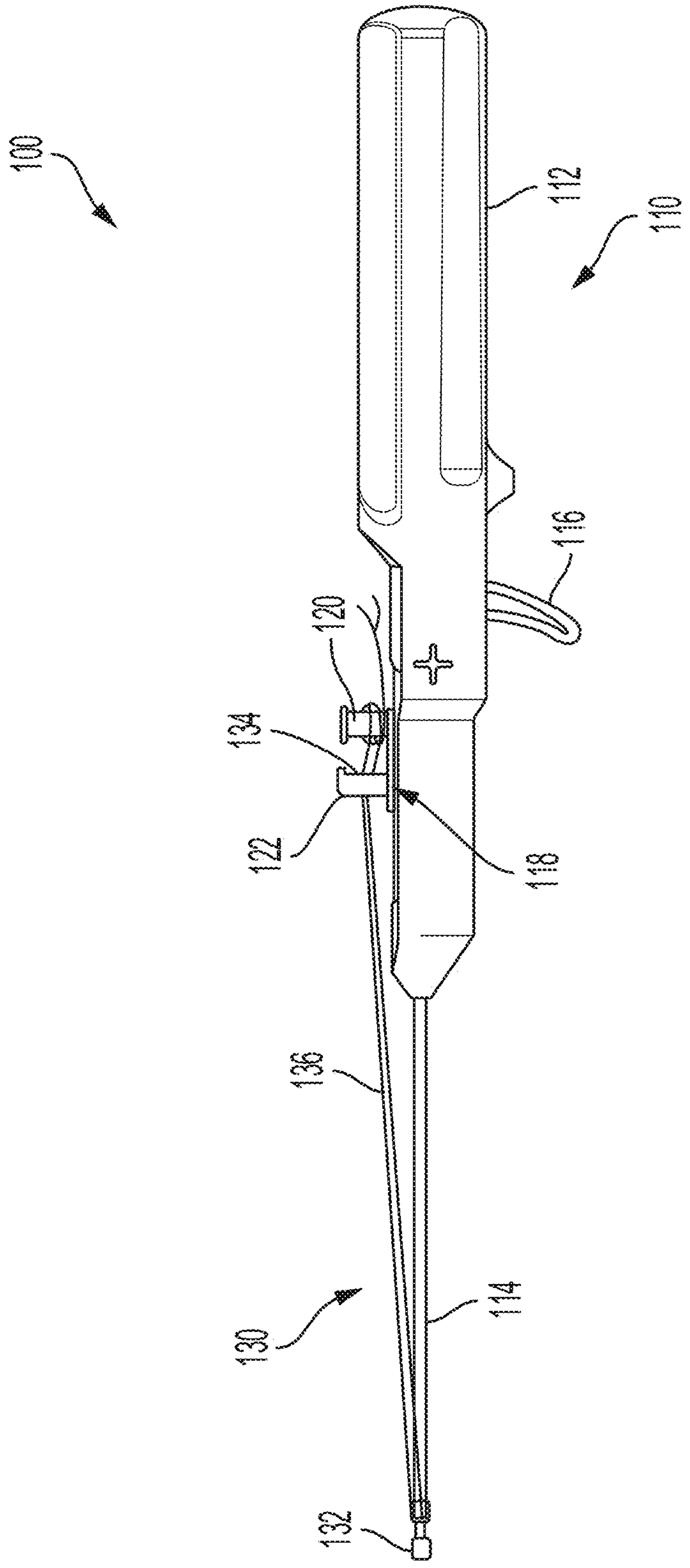
FIG. 2 illustrates a side view of the suture button inserter of FIG. 1 loaded with the suture button construct of FIG. 1 in a pre-deployment configuration, according to an aspect of the present disclosure.

FIG. 2 illustrates a loaded, or pre-deployment configuration, of the suture button insertion system 100 with the suture button construct 130 loaded onto the button inserter 110. In the pre-deployment configuration, the far bone button 132 is positioned at an end of the tube 114. In one example, a wing 804 (FIG. 8) of the far bone button 132 may be positioned within a slit formed in the end of the tube 114. The near bone button 134 is positioned against the button posts 122 and 124. In one example, a head 900 (FIG. 9) of the near bone button 134 is positioned against the button posts 122 and 124 while a peg 902 (FIG. 9) is positioned between the button post 122 and the button post 124. In aspects in which the button posts 122, 124 have a lip 414A, 414B, the lip 414A, 414B may help prevent the near bone button 134 from translating in a direction past the lip 414A, 414B prior to deployment. The suture 136 is taut, or tensioned, between the far bone button 132 and the near bone button 134 in the pre-deployment configuration. In at least some aspects, the free end of the suture 136 may be wrapped around the button posts 122 and 124 as shown.

Figure 3:
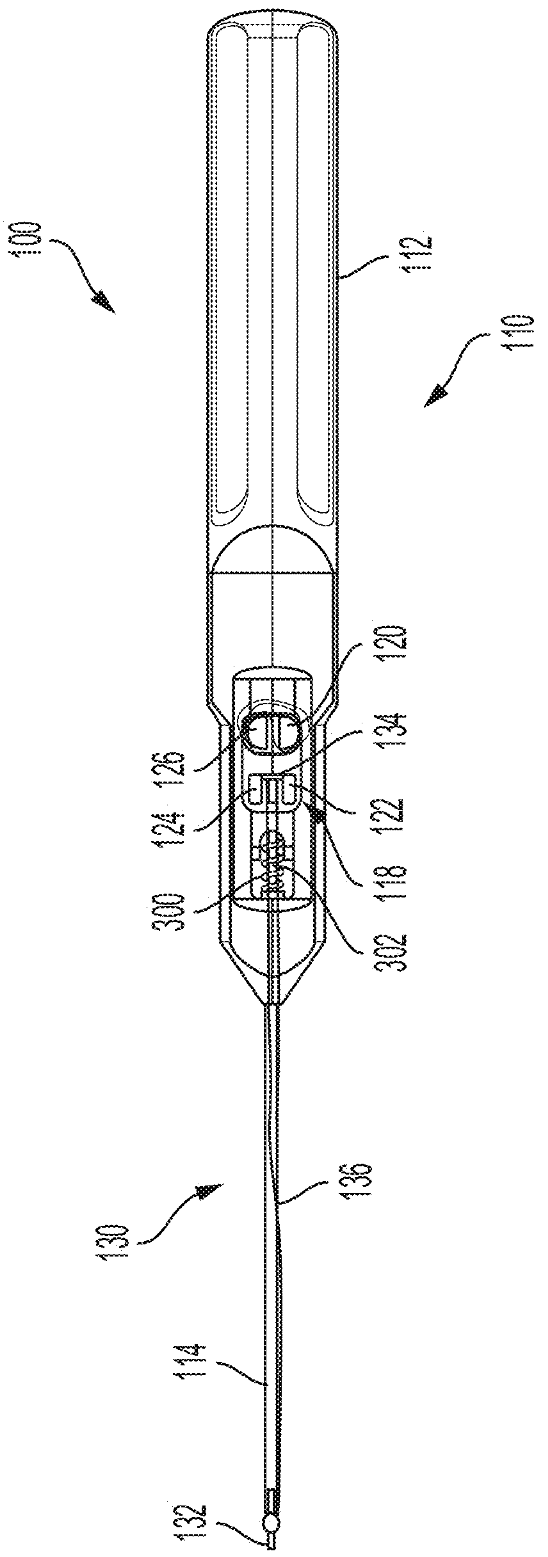
FIG. 3 illustrates a top view of the suture button inserter of FIG. 1 loaded with the suture button construct of FIG. 1 in a pre-deployment configuration, according to an aspect of the present disclosure.

FIG. 3 illustrates a top view of the suture button insertion system 100 in the pre-deployment configuration. Shown in FIG. 3 is a spring 300 positioned within the channel 140 of the handle 112. One end of the spring 300 may be in contact with the handle 112 whereas the opposite end of the spring 300 may be in contact with the body 410 of the carriage 118. In various aspects, the spring 300 may surround the rod 302. While a spring 300 is utilized in the illustrated example button inserter 110, in other examples, another suitable resilient member may be substituted for the spring 300.

In some aspects, the button inserter 110 may include one or more indicators for determining a proper location of the carriage 118 in the pre-deployment configuration. For example, FIG. 4A illustrates a magnified top view of the button insertion system 100 showing a registration window 400 of the handle 112. In such an example, the carriage 118 may include an indicator 402 that may be aligned within the registration window 400 to position the carriage 118 at a proper location. For instance, a proper location of the carriage 118 may be when the indicator 402 is positioned at the front of the registration window 400 as illustrated. In at least some aspects, a surgeon may tension the suture 136 between the far bone button 132 in the near bone button 134 and position the carriage 118 at a proper location, and then wrap the free end of the suture 136 around the suture posts 120, 126 to maintain the position of the carriage 118. In other examples, the button inserter 110 may include another suitable indicator for determining the proper location of the carriage 118.

As noted, a free end of the suture 136 may be wrapped around the suture posts 120, 126 such that the suture 136 releases from the suture posts 120, 126 without forming knots and without requiring the surgeon to loosen or unwind the suture 136. FIGS. 5A to 5G illustrate an example suture wrapping method. Only a single strand of suture 136 is shown in FIGS. 5A to 5G to help more clearly and simply illustrate the various snapshots of the example suture wrapping method; however, it will be appreciated that the free end of the suture 136 may include two separate strands of suture 136 that are wrapped in unison. Stated differently, the suture 136 shown in FIGS. 5A to 5G may be two separate strands that are wrapped as shown.

Figure 5A:
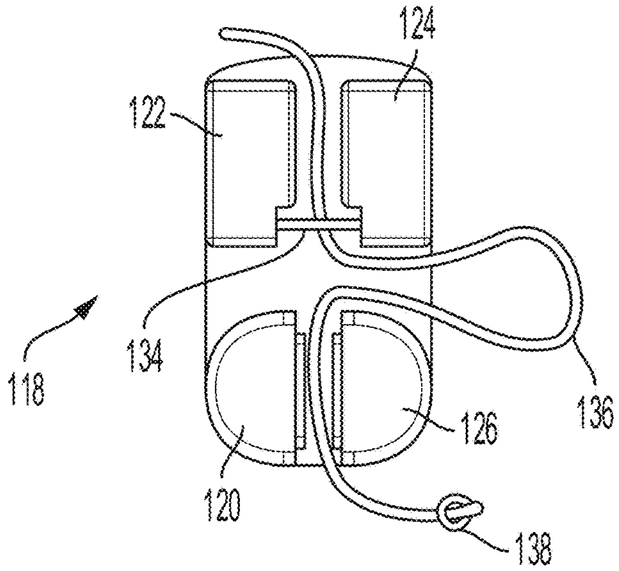
FIGS. 5A to 5G illustrate an example suture winding method, according to an aspect of the present disclosure.
Figure 5B:
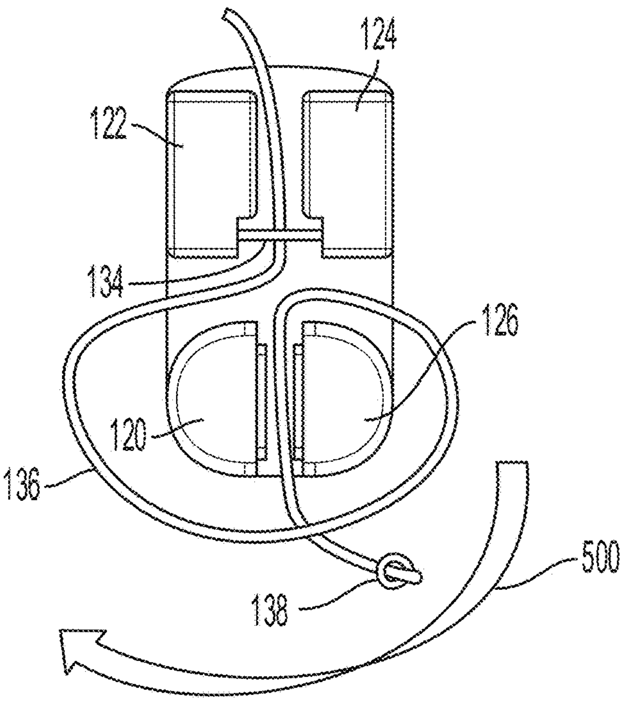
Figure 5C:
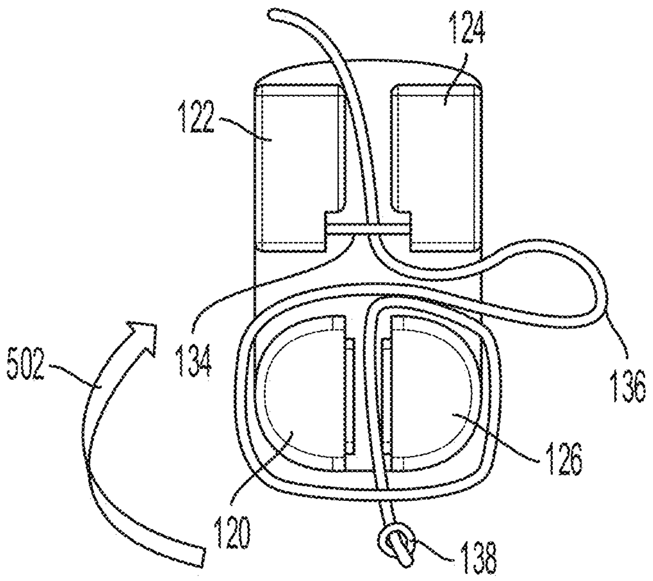
Figure 5D:
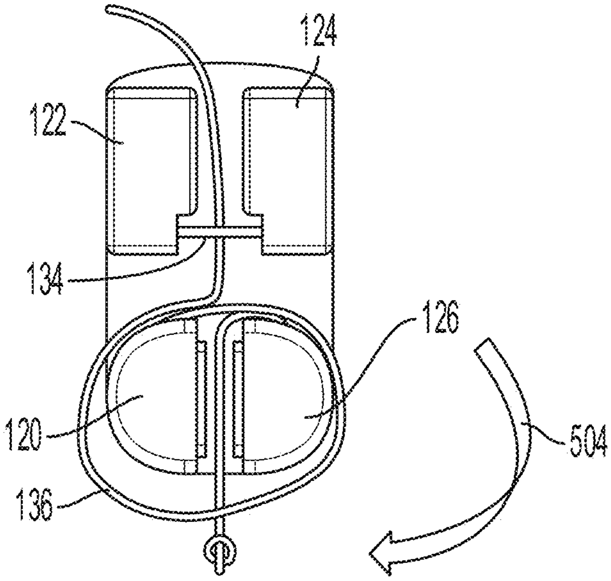
Figure 5E:
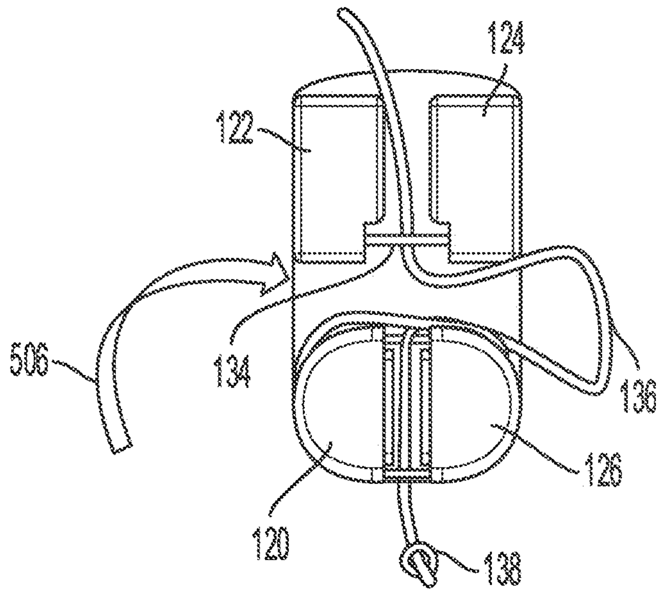
Figure 5F:
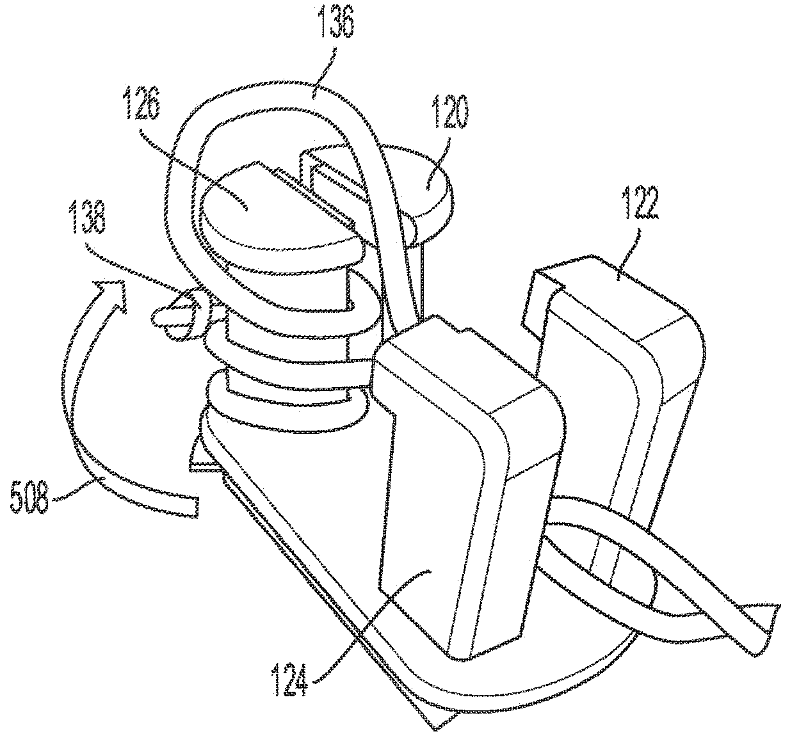
Figure 5G:
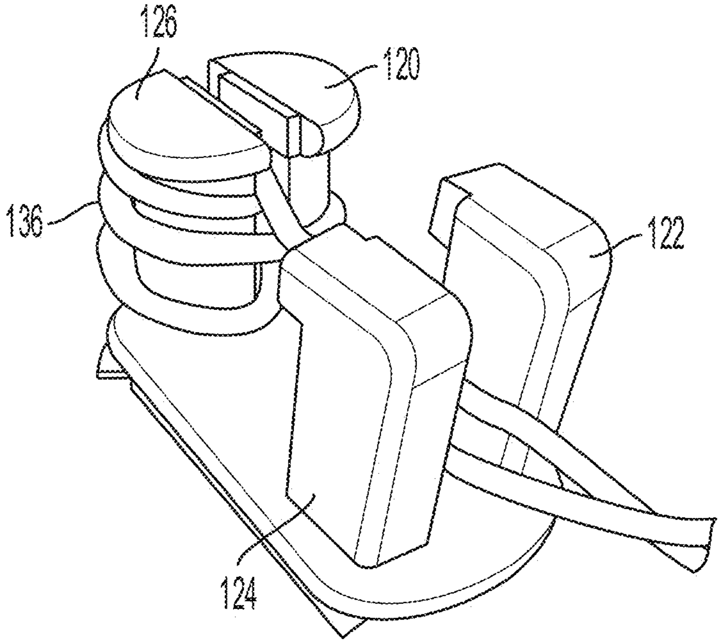

As shown in FIG. 5A, a portion of the free end of the suture 136 is first positioned between the suture post 120 and the suture post 126 while a remaining portion of the free end of the suture 136 is off to the side. As shown in FIG. 5B, the suture 136 may be wrapped in the direction of the arrow 500 thereby forming a loop of the suture 136 around the suture post 126. As shown in FIG. 5C, the suture 136 may be wrapped in the direction of the arrow 502 around the outside of the suture post 120 and then in the direction of the arrow 504 around the outside of the suture post 126, as shown in FIG. 5D, thereby forming a loop of the suture 136 around both the suture post 120 and the suture post 126. As shown in FIG. 5E, the suture 136 may then be wrapped in the direction of the arrow 506 around the outside of the suture post 120. As shown in FIG. 5F, the suture 136 may then be wrapped in the direction of the arrow 508 such that the portion of the suture 136 currently being wrapped is wrapped around the outside of the suture post 126 while the suture 136 coming from the button 134 is positioned between the suture post 120 and the suture post 126, thereby forming a loop around the suture post 126. FIG. 5G shows a final configuration of the wrapped suture 136.

A release mechanism for deploying the near bone button 134 from the example button inserter 110 will now be described. A surgeon may first transport the far bone button 132 through formed bone holes in a first and second bone using the button inserter 110. Once through the formed bone holes, the surgeon may deploy the far bone button 132 from the button inserter 110. For example, the surgeon may actuate the trigger 116 to deploy the far bone button 132. The deployed far bone button 132 positions itself against the far bone with tension in the suture 136 holding the far bone button 132 against the far bone. With the far bone button 132 deployed, the near bone button 134 may then be deployed.

Figure 6:
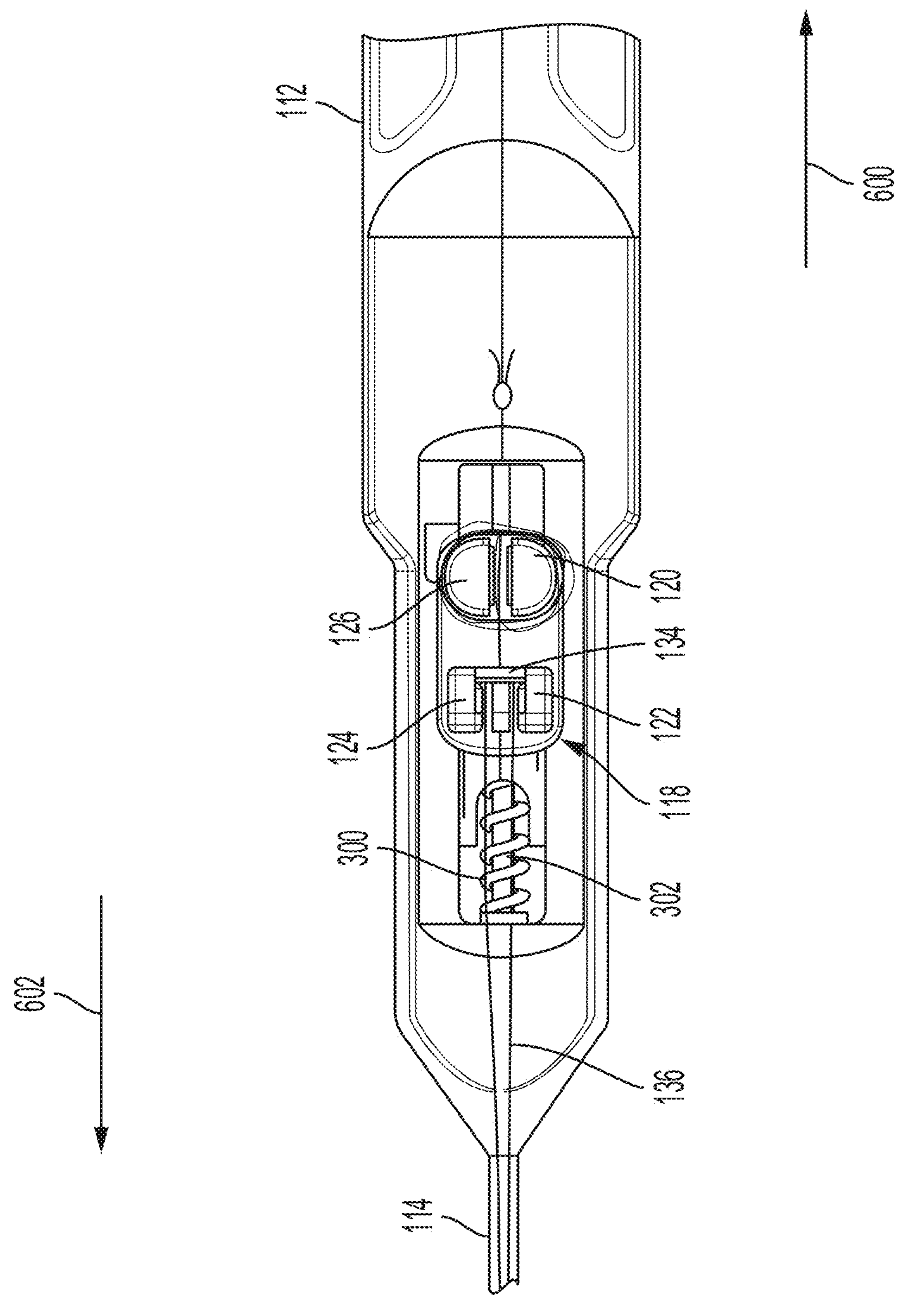
FIG. 6 illustrates a magnified view of the top view of FIG. 3 showing a deployment mechanism of the suture button inserter, according to an aspect of the present disclosure.

FIG. 6 illustrates a magnified top view of a portion of the suture button insertion system 100 after the far bone button 132 has been deployed from the button inserter 110. The surgeon may translate the handle 112 of the button inserter 110 away from the deployed far bone button 132 in the direction of the arrow 600. As the handle 112 is translated in the direction of the arrow 600, tension in the suture 136 prevents the carriage 118 from translating with the handle 112. Stated differently, the carriage 118 remains at least relatively stationary as the handle 112 is translated in the direction of the arrow 600 such that a position of the carriage 118 changes with respect to the channel 140 of the handle 112. The movement of the handle 112 in the direction of the arrow 600 while the carriage 118 remains stationary thereby compresses the spring 300 between the handle 112 and the carriage 118.

As the handle 112 is translated in the direction of the arrow 600 and the position of the carriage 118 changes with respect to the channel 140, a point is reached when the protrusions 412A, 412B of the carriage 118 are aligned with the notches 704A, 704B of the handle 112. At this point, a threshold amount of tension in the suture 136 forces the carriage 118 to change orientation with the protrusions 412A, 412B traveling through the notches 704A, 704B. For instance, tension in the suture 136 applies a force in the direction of the arrow 602 to the carriage 118. The force from the tension in the suture 136 at the level of the button posts 122, 124 (e.g., off-center relative to the body 410 of the carriage 118) induces rotation of the carriage 118. At the same time, an initial change in orientation of the carriage 118 induces a release of the compressed spring 300, which applies a force in the direction of the arrow 600 to the carriage 118. The counteracting force from the spring 300 (e.g., the direction of the arrow 600 is opposite the direction of the arrow 602) is in a different plane than the plane in which the force from the tension in the suture 136 resides, which thereby further induces rotation of the carriage 118.

In various aspects, the combination of the counteracting forces from the tension in the suture 136 and the spring 300 induces the carriage 118 to rotate about ninety degrees. For instance, the carriage 118 may rotate from a horizontal orientation shown in FIG. 2 to a vertical orientation shown in FIG. 7. The change in orientation of the carriage 118 releases the near bone button 134 from the carriage 118. For instance, the button posts 122, 124 no longer restrain the near bone button 134 against the tension in the suture 136 with the carriage 118 in the vertical orientation. Further, the vertical orientation of the carriage 118 loosens the tension in the suture 136 on the near bone button 134 thereby releasing the near bone button 134 from the carriage 118. Stated differently, the change in orientation of the carriage 118 in combination with the loosening tension in the suture 136 allows the near bone button 134 to separate from the button posts 122, 124 and release from the carriage 118.

As noted above, the carriage 118 may be positioned in a proper location in the pre-deployment configuration. The proper location of the carriage 118 in the pre-deployment configuration enables the counteracting forces from the tension in the suture 136 and the spring 300 to induce the change in orientation of the carriage 118 when the protrusions 702A, 702B are aligned with the notches 704A, 704B. Stated differently, in the pre-deployment configuration, the carriage 118 is positioned such that when the handle 112 is translated to deploy the near bone button 134, a threshold amount of tension is generated in the suture 136 when the protrusions 412A, 412B of the carriage 118 are aligned with the notches 704A, 704B.

As the near bone button 134 deploys from the carriage 118, and the handle 112 is further translated away from the deployed far bone button 132 (e.g., in the direction of the arrow 600), the free end of the suture 136 releases, or unwinds, from the suture posts 120, 126. The example suture wrapping method illustrated in FIGS. 5A to 5G allows the suture 136 to freely unwind from the suture posts 120 and 126 without forming a knot(s) as the near bone button 134 is deployed from the carriage 118 and the button inserter 110 is moved away from the deployed near bone button 134.

Figure 7:
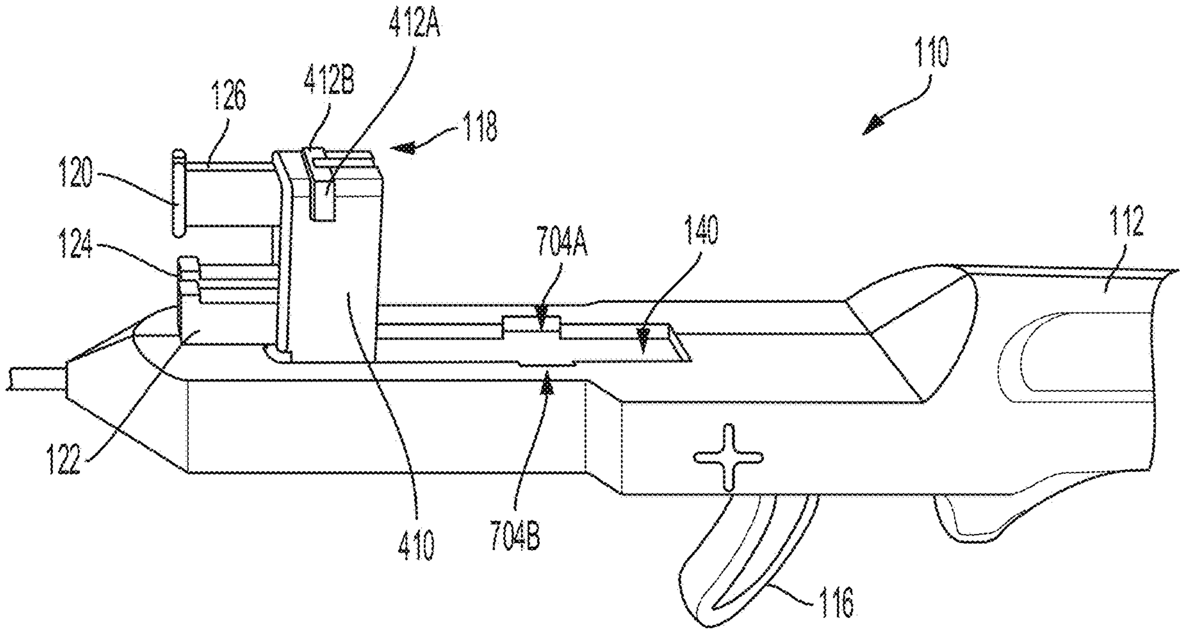
FIG. 7 illustrates a perspective view of the suture button inserter of FIG. 1 in a post-deployment configuration, according to an aspect of the present disclosure.

FIG. 7 illustrates the button inserter 110 with the carriage 118 in a vertical orientation after deployment of the suture button construct 130.

Accordingly, a surgeon may deploy the near bone suture button 134 and accompanying suture 136 in the suture button construct 130 from the button inserter 110 in a single motion by translating the button inserter 110 away from a deployed far bone button 132. In this way, the suture button insertion system 100 helps eliminate the manual process of loosening or unwrapping the suture 136 and removing the near bone button 134 required of surgeons using typical button inserters. As such, the button inserter 110 more effectively and efficiently deploys the near bone button 134 than typical button inserters.

Figure 8:
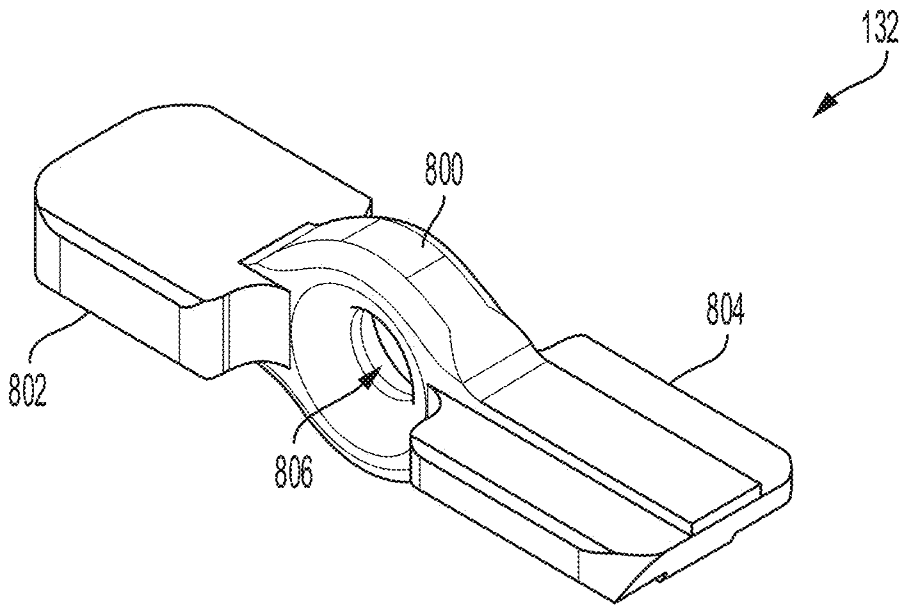
FIG. 8 illustrates a perspective view of an example far bone button, according to an aspect of the present disclosure.

FIG. 8 illustrates a perspective view of an example far bone button 132. In this example, the far bone button 132 may include a base 800 integral to or connected with a wing 802 and a wing 804 that extends from the base 800. An opening 806 through which suture is routed may be defined by the base 800 of the example far bone button 132. In other examples, the far bone button 132 may have other suitable configurations.

Figure 9:
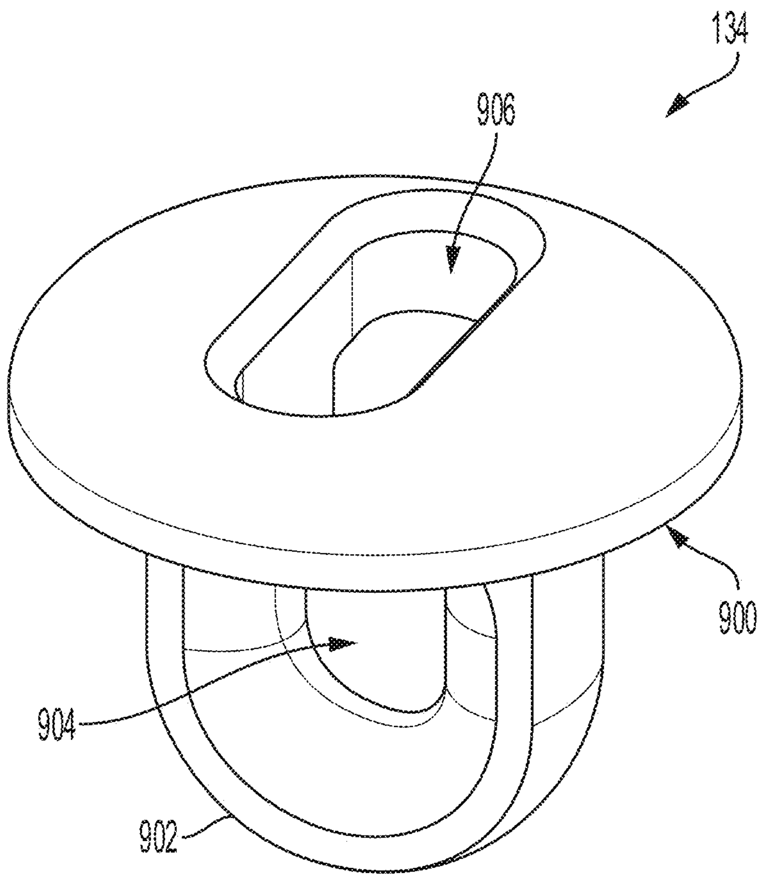
FIG. 9 illustrates a perspective view of an example near bone button, according to an aspect of the present disclosure.

FIG. 9 illustrates a perspective view of an example near bone button 134. In this example, the near bone button 134 may include a head 900 integral with or attached to a peg 902. The peg 902 may define an opening 904 through which suture may be routed. The head 900 includes an opening 906 through which suture may be routed. In other examples, the near bone button 134 may have other suitable configurations.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A method for deploying a suture button construct from a button inserter, the suture button construct including a far bone button joined by a suture to a near bone button, the method comprising: inserting the far bone button through a bone hole via the button inserter; deploying the far bone button from the button inserter; translating the button inserter away from the far bone button which thereby deploys the near bone button from the button inserter; and pushing upward on a portion of the button inserter to release the near bone button from the button inserter.

2. The method of claim 1, wherein a free end of the suture is coupled to the button inserter, and wherein translating the button inserter away from the far bone button further deploys the free end of the suture from the button inserter.

3. The method of claim 1, further comprising wrapping a free end of the suture around two posts of the button inserter prior to inserting the far bone button through the bone hole.

4. The method of claim 3, wherein the two posts comprise a first post and a second post, and wherein wrapping the free end of the suture around the two posts of the button inserter comprises:

wrapping the suture on the first post; and wrapping the suture around the second post.

5. The method of claim 3, wherein the two posts comprise a first post and a second post, and wherein wrapping the free end of the suture around the two posts of the button inserter comprises:

positioning a portion of the free end between the first post and the second post; and subsequent to positioning the portion of the free end between the first post and the second post, forming a first loop of the suture around the first post.

6. The method of claim 5, further comprising, subsequent to forming the first loop of the suture around the first post, forming a second loop around the first post and the second post.

7. The method of claim 6, further comprising:

subsequent to forming the second loop, wrapping the suture around an outside of the second post; and subsequent to wrapping the suture around the outside of the second post, wrapping the suture around an outside of the first post while a portion of the suture coming from the near bone button is positioned between the first post and the second post.

8. The method of claim 7, wherein the suture comprises two separate strands of suture and wherein the method comprises wrapping the two separate strands in unison.

9. The method of claim 1, further comprising loading the suture button construct onto the button inserter.

10. The method of claim 1, further comprising tensioning the suture after deployment of the near bone button.

11. The method of claim 10, further comprising securing the near bone button after tensioning by tying off the suture.

12. The method of claim 1, wherein the near bone button comprises a head and a peg, wherein the peg defines an opening through which the suture is routed.

13. The method of claim 1, wherein the bone hole is formed in an ankle bone and wherein the method comprises repairing a syndesmosis injury.

14. The method of claim 1, wherein deploying the far bone button from the button inserter comprises actuating a mechanism for deploying the far bone button.

15. The method of claim 1, wherein translating the button inserter away from the far bone button comprises moving the button inserter partially back through the bone hole.

* * * * *